United States Patent [19]
Cooker

[11] Patent Number: 5,338,289
[45] Date of Patent: Aug. 16, 1994

[54] SPINAL SUPPORT FOR RECLINING PERSONS

[76] Inventor: John T. Cooker, 220 S. Nashville Ave., Tucson, Ariz. 85747

[21] Appl. No.: 38,487

[22] Filed: Mar. 29, 1993

[51] Int. Cl.⁵ .................................................. A61F 5/02
[52] U.S. Cl. ..................................... 602/19; 128/99.1
[58] Field of Search .......................... 602/18, 19, 23; 128/95.1, 96.1, 100.1, 120.1, 118.1

[56] References Cited

U.S. PATENT DOCUMENTS

| | | | |
|---|---|---|---|
| 820,380 | 5/1906 | Beatty . | |
| 3,315,670 | 4/1967 | Fumea . | |
| 4,294,239 | 10/1981 | Oram et al. | 128/96.1 |
| 4,702,235 | 10/1987 | Hong | 602/13 |
| 4,991,572 | 2/1991 | Chases | 602/13 |
| 4,991,573 | 2/1991 | Miller | 602/19 |
| 5,037,436 | 8/1991 | Heaston | 623/7 |
| 5,060,639 | 10/1991 | Marcus | 602/19 |
| 5,062,414 | 11/1991 | Grim | 602/19 |
| 5,111,807 | 5/1992 | Spahn et al. | 606/244 |
| 5,143,057 | 9/1992 | DePasquale | 602/19 X |
| 5,211,623 | 5/1993 | Sarkozi | 602/18 |

Primary Examiner—Richard J. Apley
Assistant Examiner—Beverly A. Meindl
Attorney, Agent, or Firm—Richard C. Litman

[57] ABSTRACT

A spinal support pad for use by persons reclining or sleeping provides support for the lumbar area and side regions of the waist. The normally concave areas of the body tend to sag when a person is lying on a firm or semi-resilient surface, such as a standard mattress, resulting in abnormal spinal curvature, e.g., lordosis and/or scoliosis and resulting muscular pain and distress. The support pad of the present invention provides support for the body in these areas, preventing undue curvature of the spine and the problems associated with such undue curvature. The support pad comprises a support portion and belt portion, with the two portions combining to encircle the waist area of the user; the support portion forms the majority of the total circumference of the device. The belt portion may be joined to each end of the support portion, or may pass through a pocket within the support portion to divide the support portion into two pockets, each containing a pad. The pads may be formed of a variety of materials, such as natural or synthetic fiber, resilient foam, gel, or may be pneumatically inflated. The pad(s) is/are removable from the rest of the device to provide for the washing or other cleaning of the device.

14 Claims, 2 Drawing Sheets

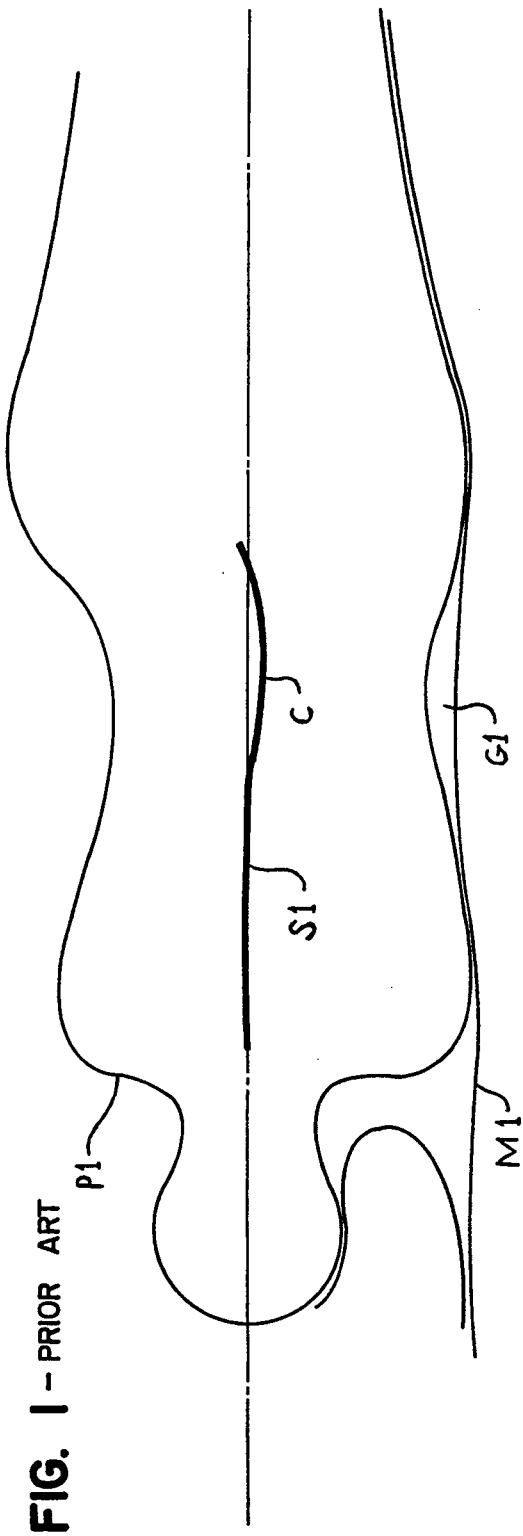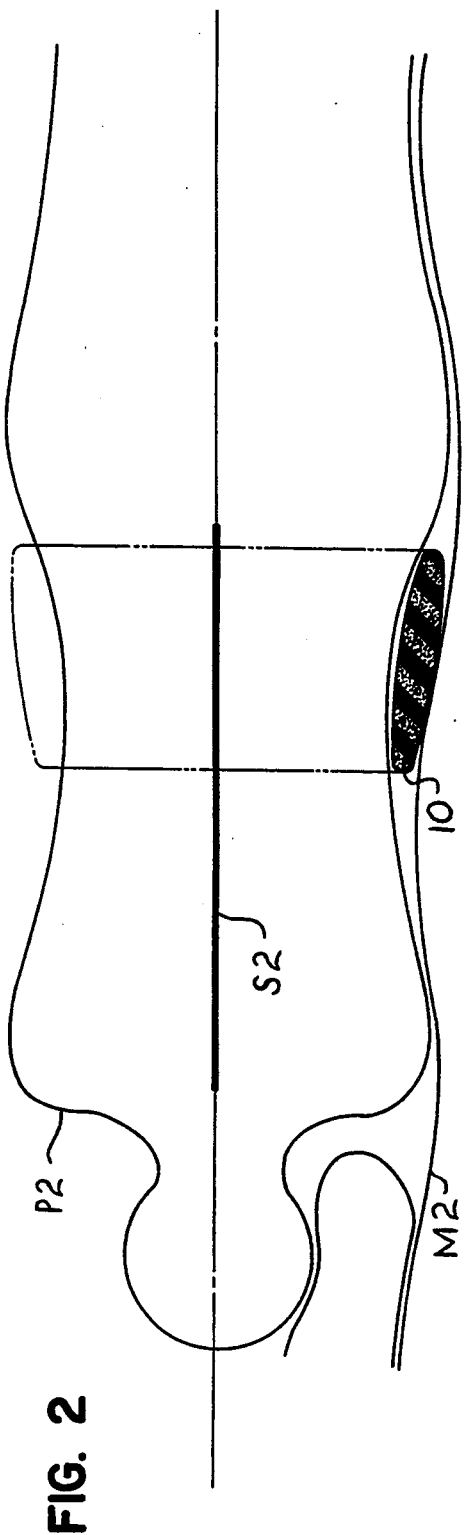

SPINAL SUPPORT FOR RECLINING PERSONS

FIELD OF THE INVENTION

The present invention relates generally to supports and the like for the body, and more specifically to a padded belt which may be worn around the waist, to support the normal body concavities of the waist and lumbar region when a person is reclining or sleeping.

BACKGROUND OF THE INVENTION

Some authorities have held that lower and other back problems began to bother people when humans first evolved into bipedal beings. Complaints of back problems, particularly in the lower back or lumbar region, are nearly universal among people, and as a result a multitude of remedies have been developed. Many of these remedies are in the form of braces or supports, intended to relieve muscle strain and pain in the lower back for erect or seated persons.

In addition, many authorities have expressed concern over the support (or lack thereof) provided by the standard mattress. The relatively wide hips and buttocks of a person, in contrast with a relatively narrow waist, results in concentrations of pressure at the hips and buttocks when a person is reclining or sleeping and a corresponding lack of pressure or support at the small of the back (for persons lying on their back) and at the waist (for persons lying on their side). Many people hold that this results in a sagging of the spine and central body in the area of the waist, and abnormal curvature of the spine (lordosis and/or scoliosis) and consequent muscular strain and resultant pain.

As a result, various different mattresses and beds have been developed in attempts to alleviate the above problems. Air mattresses and waterbeds have been found to provide some limited relief for the above problems, due to their relatively uniform distribution of the pressures of a reclining person. However, these devices do not provide a universal solution, due to the very distribution of pressure which they provide: It can be difficult for a bedridden person to arise from, or even change position in, such a bed due to the cushioning provided.

Some persons have experimented with pillows or other padding in combination with a standard bed to provide the additional support needed at the waist. However, pillows and the like do not move with a person when he/she moves in the bed; thus, any relief provided by such a pad will only be good until the person changes his/her position in the bed.

The need arises for a spinal support for reclining persons, which device provides the spinal support needed no matter what the position of the person using the device. The support should be lightweight and comfortable, and be easily washable or cleanable as needed. Finally, the support must also be adaptable to persons of varying size or stature, to provide optimum utility.

DESCRIPTION OF THE PRIOR ART

U.S. Pat. No. 820,380 issued to John H. Beatty on May 8, 1906 discloses a Garter having a pneumatically inflated semi-encircling element. The device is intended for use in the manner of a standard garter, i.e., to encircle the thigh. It is of relatively narrow construction, and would fail to provide the lateral and dorsal support required for use in the manner of the present invention, by a reclining person.

U.S. Pat. No. 3,315,670 issued to Judith G. Fumea on Apr. 25, 1967 discloses a Maternity Belt for use by women for resting or sleeping on their sides. The device includes two wedge shaped pads which provide lateral support for the distended abdomen of a woman in late pregnancy, if the woman wishes to lie upon her side. No dorsal support is provided, and little lateral support is provided at the waist rearward from the sides of the abdomen.

U.S. Pat. No. 4,702,235 issued to James K. Hong on Oct. 27, 1987 discloses a Therapeutic Inflatable Lumbar Brace Having A Heater. The device provides a relatively narrow pneumatically inflated lumbar cushion including a heating element. The shape of the device and lack of lateral support precludes comfortable support for a reclining person.

U.S. Pat. No. 4,991,572 issued to Ronald L. Chases on Feb. 12, 1991 discloses a Lumbar Traction Device providing for the lifting support of a patient suspended therein. Among other differences, the discontinuities between the triangular lateral support areas and the central area render the device uncomfortable for sleeping, as do the air valve and the rings attaching the support strap.

U.S. Pat. No. 4,991,573 issued to Donald L. Miller on Feb. 12, 1991 discloses an Orthopedic Support Belt including a semi-rigid extension pad. The resulting device is more suited for use by an erect person; little or no support is provided for the lateral waist and lumbar areas of a reclining person.

U.S. Pat. No. 5,037,436 issued to Sharon K. Heaston on Aug. 6, 1991 discloses a Breast Prosthesis And Support Therefor. The device is a pneumatically inflatable toroid for the support of the prosthesis when it is removed from the wearer. The size, as well as the uniform toroidal shape, render it unsuitable for use in the environment of the present invention.

U.S. Pat. No. 5,060,639 issued to Donna Marcus on Oct. 29, 1991 discloses a Back Support having a plurality of stitched together areas providing different degrees of stiffness. The back support portion further adjoins lateral side support portions. The resulting device is intended for erect or seated persons, and lacks the necessary thickness and continuity for use in the environment of the present invention.

U.S. Pat. No. 5,062,414 issued to Tracy E. Grim on Nov. 5, 1991 discloses a Simplified Orthopaedic Back Support including plural pneumatically inflated or gel filled chambers which function to provide additional rigidity for the back of a wearer of the article when the wearer is erect or sitting. The attachment means extends from each end of the support, rather than passing completely through and around the support.

Finally, U.S. Pat. No. 5,111,807 issued to James G. Spahn et al. on May 12, 1992 discloses a Back Belt having a single pneumatic chamber in the manner of other devices discussed above. A special joint means is disclosed for the attachment of the belt portion to the remaining portion of the belt.

None of the above noted patents, taken either singly or in combination, are seen to disclose the specific arrangement of concepts disclosed by the present invention.

SUMMARY OF THE INVENTION

By the present invention, an improved spinal support for reclining persons is disclosed.

Accordingly, one of the objects of the present invention is to provide an improved spinal support which is capable of providing support for the concave lateral waist areas and the concave lumbar area of the body of the wearer while reclining.

Another of the objects of the present invention is to provide an improved spinal support which serves to preclude undue spinal curvature, such as lordosis and/or scoliosis, in the wearer.

Yet another of the objects of the present invention is to provide an improved spinal support at least the outer cover of which is washable.

Still another of the objects of the present invention is to provide an improved spinal support which may include cushions of open or closed cell foam, fiber material, or may be pneumatically inflated or gel filled as desired.

A further object of the present invention is to provide an improved spinal support which forms a continuous and seamless surround of the sides of the waist and the small of the back of the wearer.

An additional object of the present invention is to provide an improved spinal support which includes a central belt or securing portion with pockets for the containment of padding to either side thereof.

Another object of the present invention is to provide an improved spinal support which provides for a padding material of different dimensions and/or densities within two different pockets.

Yet another object of the present invention is to provide an improved spinal support which includes padding of greater thickness at the areas adjacent to the small of the back and the sides of the waist of the wearer.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

FIG. 1 is a side view of a reclining person, demonstrating the deficiencies of the support developed by a conventional mattress.

FIG. 2 is a side view of a reclining person, showing the use of the present invention to provide the support needed.

Similar reference characters denote corresponding features consistently throughout the several figures of the attached drawings.

DETAILED DESCRIPTION OF THE PREFERRED EMBODIMENTS

Referring now particularly to FIG. 2 of the drawings, the present invention will be seen to relate to a spinal support 10 for use by reclining or sleeping persons P2. The prior art shown in FIG. 1 represents a person P1 sleeping or reclining on their side on a mattress M1 or other like resilient surface. The problem with such surfaces as a mattress M1 is that when they are provided with sufficient firmness for adequate support, they generally are incapable of fully conforming to the curvature of the human body, particularly in the concave areas of the lumbar region (the small of the back) and ground the sides of the waist between the hips and shoulders. This lack of support will allow the body to sag downward into the gap G1, as shown in FIG. 1, with a resulting lateral curvature C of the spine S1. While FIG. 1 shows a gap G1 between the side of the waist of a person P1 and the mattress M1, it will be understood that a supine person will suffer a like problem due to the concave area between the lumbar area of the spine and a mattress also; the present invention responds to such a situation as well as the one shown in FIGS. 1 and 2.

The resulting abnormal curvature of the spine S1 will often result in muscular pain and stiffness for a person when they arise, particularly if they have previously suffered some back injury or do not have extremely good muscle tone in the waist, back and hip areas. On the other hand, the spinal support 10 shown in section in FIG. 2 eliminates such a gap G between the waist or lower back of a reclining person, and provides support to that area of the body. It will be seen that the support 10 schematically illustrated in FIG. 2 eliminates the sag in the spine shown in FIG. 1, as shown by S2 by means of supporting the concave waist (or lower back) area(s) of the body during reclining or sleeping an mattress M2 when fastened around the person P2 to form a circumferential toroidal support around the waist area of person P2.

Figure 3:
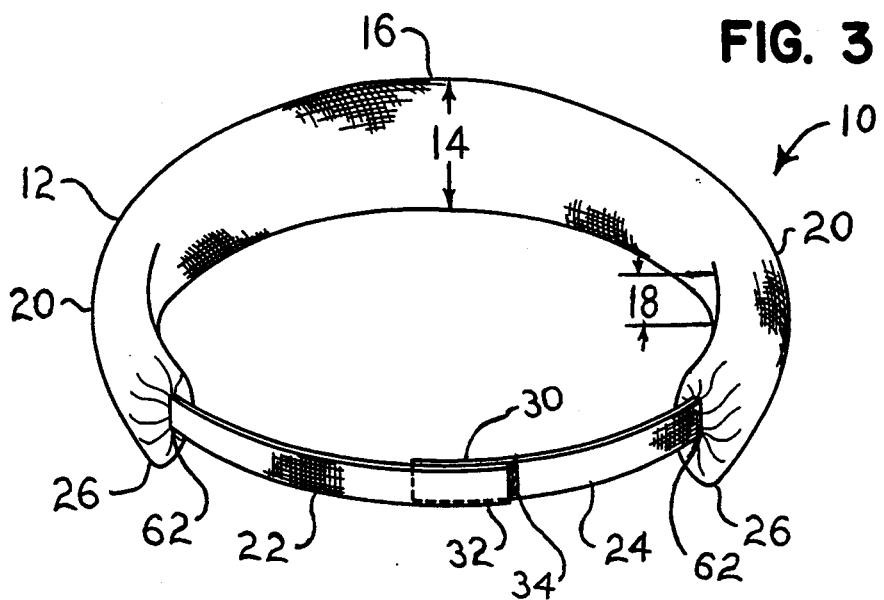
FIG. 3 is a front perspective view of the present invention.
Figure 4:
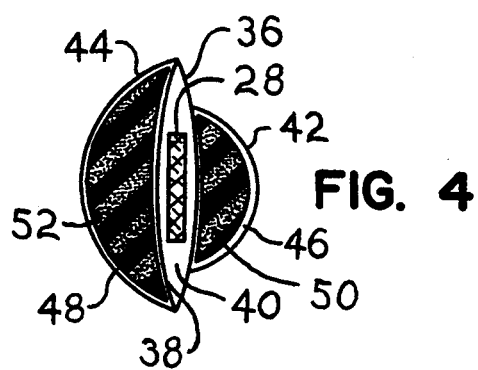
FIG. 4 is a cross-sectional view of the present invention.
Figure 5:
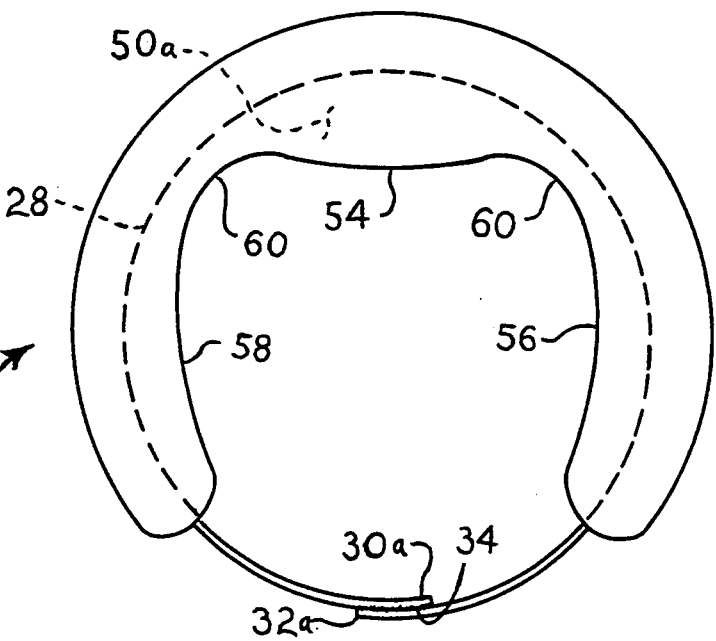
FIG. 5 is a top plan view of another embodiment of the present invention, showing the variation in thickness of the pad material for better support.

FIGS. 3 through 5 illustrate various embodiments and construction details of the present invention. FIG. 3 provides a general view of the support 10 of the present invention, showing the three quarter circumferential surrounding of the padded area 12. It will be further noted that although the padded area 12 is formed with no discontinuities, the width 14 is greater at the median 16 of pad 12 than the width 18 to either side 20. Thus, a wider area of support is provided by the median area 16 of pad 12, for the lumbar area or small of the back of a reclining person; the lower edge of the wider area 14 may be positioned beneath the sacral area of the spine as desired for proper comfort. Two short belt lengths 22 and 24 of a lightweight fabric or other suitable material are secured to the ends 26 of the padded area 12 of support 10, or alternatively a single belt 28 may pass completely through the length of the support, as shown in FIGS. 4 and 5. The mating ends 30 and 32 of belt lengths 22 and 24, or 30a and 32a of the single belt 28, are preferably provided with fastening means allowing the two mating ends to lie flat relative to one another and in close contact, so as not to form an uncomfortable lump should the person wearing support 10 turn to a prone position. Hook and loop fabric material 34 (e.g., VELCRO) has been found suitable.

FIG. 4 illustrates the internal construction of spinal support 10. Two layers of material 36 and 38 are used to form a belt pocket 40 extending the length of pad 12. A third layer of material 42 of relatively narrower width is secured to the first layer 36, and a fourth layer 44 of full width is secured to the upper and lower periphery of the second layer 38. It will be seen that the first and third layers 36 and 42 combine to form a first pad pocket 46, while the second and fourth layers 38 and 44 combine to form a second pad pocket 48. First through fourth layers 36, 38, 42, and 44 are preferably formed of a relatively soft, lightweight and pliable fabric material for comfort while being worn and further providing for washing or cleaning of the material. By providing two pad pockets 46 and 48, several advantages are obtained: (1) the belt 28 is centrally disposed between the two pockets 46 and 48, thereby providing greater strength and durability for spinal support 10; (2) the different widths of the two pockets 46 and 48 provide for the inversion of support 10 relative to the body of the user, to adjust for different comfort needs; (3) different materials or means may be used to pad the two pockets 46 and 48, thereby providing further adjustability in the comfort of the support 10; and (4) the two pockets 46 and 48 may be filled or padded to a greater or lesser degree to adjust the comfort of support 10. Any or all of the above variations may be used in combination as desired.

The first and second pads 50 and 52 may be formed of a variety of materials, such as natural or synthetic fiber, open or closed cell foam material, a viscous gel, or may be pneumatically inflated. Different shapes may be provided for the foam material, such as ridged or other shapes, to further adjust the support and comfort provided. The semicircular or lenticular shape of pads 50 and 52 shown in FIG. 4 may be used to form such pads capable of maintaining a given shape, such as those formed of foam or other like material. As noted above, various combinations of the above may be used in each of the two pockets 46 and 48 to adjust the comfort of support 10 as desired. For example, it may be found for a particular user that a relatively dense fibrous material pad 50 may provided additional support when installed within the narrower first pad pocket 46, and that a pneumatically inflated or gel filled pad 52 installed in the second pad pocket 48 may provide for the more comfortable spreading of the pressure developed by such a dense pad 50. A multitude of variations are feasible using the support of the present invention, as noted above.

FIG. 5 discloses an alternate embodiment, wherein a support 10a includes a first pad 50a having a variable thickness, in order to provide a maximum thickness at those areas requiring such as at the lumbar area 54 and left and right side waist areas 56 and 58. The transition areas 60 may be relatively thin, as little thickness is required at those areas 60. Support 10a thus provides the additional thickness needed to support the lumbar area of the spine by means of area 54 when a person using support 10a is in a supine position, and further provides the additional thickness needed at the left and right concave areas of the waist between the rib cage and the pelvis by means of the relatively thick areas 56 and 58 at the left and right sides of the waist area when a person is lying on their left or right side.

Support 10 or 10a is used by securing the belt ends 30 and 32, or 30a and 32a, at the front of the user thereby to position the left and right lateral areas 20 and 56 and 58 respectively adjacent the left and right sides of the waist, and to position the lumbar area 16 or 54 adjacent the lumbar area or small of the back of the user. When the user of support 10 or 10a then reclines on a mattress M or other semi-resilient pad, the additional support provided by areas 16, 20, 54, 56 or 58 as appropriate will prevent the sagging of the supported area of the body of the user and thus keep the spine of the user straight, thereby preventing undue muscle strain and resulting aches and pain upon arising. As the wearer of support 10 or 10a turns while resting, the support 10 or 10a will turn with him or her by means of being secured about the waist by the belt ends 22 and 24 or belt 28, thereby always providing the appropriate support needed no matter what the position of the reclining user of support 10 or 10a.

Support 10 or 10a may be worn over the other clothing, pajamas or other night wear, etc., or alternatively may be worn beneath such clothing and immediately adjacent the skin as desired. The preferably soft fabric covering provides the comfort needed in such circumstances, and the various pads or support inserts 50 and 52 therein may be removed in order that the remaining elements of support 10 or 10a may be washed or otherwise cleaned as needed closure means 62 at the ends 26 of support 10 (FIG. 3), such as tucking in the ends of the fabric pocket material as shown or other suitable means, may be used to secure the pads or inserts 50 and 52 within the support 10 or 10a as required or desired.

It is to be understood that the present invention is not limited to the sole embodiment described above, but encompasses any and all embodiments within the scope of the following claims.

I claim:

1. A spinal support for spinal alignment use by a person reclining upon a surface, said spinal support comprising:
   a padded support portion having a median portion and left and right side portions continually formed with sufficient thickness to prevent sagging of the supported area of the person's body,
   said padded support portion including at least one support pad disposed therein, said at least one support pad being removable from said padded portion;
   a belt portion comprising first and second mating ends extending respectively from said left and right side portions of said padded support portion; and
   said belt portion and said support portion forming a toroid when said first and second ends of said belt portion are joined together, with said support portion comprising the majority of said toroid, whereby,
   said spinal support is secured around the waist of a person by means of said first and second mating ends of said belt portion with said median portion of said padded support portion adjacent the lumbar area of the person and said left and right side portions of said padded portion respectively adjacent the left and right sides of the waist area of the person, thereby providing additional support between the lumbar area and the left and right sides of the waist area of the person and the surface to prevent sagging while the person is reclining on the surface for spinal alignment.

2. The spinal support of claim 1 wherein:
   said median portion of said padded portion has a greater width than said left and right portions of said padded portion, whereby
   additional support is provided to the sacral area of a person wearing said spinal support by means of said greater width of said median portion.

3. The spinal support of claim 1 wherein:
   said median portion of said padded portion and said left and right portions of said padded portion include transition areas therebetween, with said median portion and said left and right portions of said padded portion having thicknesses relatively greater than said transition areas.

4. The spinal support of claim 1 wherein:

said at least one support pad is formed of an open cell foam material.

5. The spinal support of claim 1 wherein:
said at least one support pad is formed of a closed cell foam material.

6. The spinal support of claim 1 wherein:
said at least one support pad is formed of a natural fiber material.

7. The spinal support of claim 1 wherein:
said at least one support pad is formed of a synthetic fiber material.

8. The spinal support of claim 1 wherein:
said at least one support pad contains a viscous gel material.

9. The spinal support of claim 1 wherein:
said at least one support pad is pneumatically inflated.

10. A spinal support for spinal alignment use by a person reclining upon a surface, said spinal support comprising:

a padded support portion having a median portion and left and right side portions continually formed with sufficient thickness to prevent sagging of the supported area of the person's body, wherein;

said padded support portion comprises a belt pocket formed of a first and second layer of material, with a third and a fourth layer of material respectively secured to said first and said second layers of material to form respectively a first and a second pad pocket disposed to the outside of said belt pocket on opposite sides thereof;

said first and said second pad pockets each contain a support pad;

said belt portion passes continually through said belt pocket with said first and second ends of said belt portion extending from said belt pocket to provide for the securing of said spinal support about a person by means of said first and second mating ends of said belt portion, said belt portion and said support portion forming a toroid when said first and second ends of said belt portion are joined together, with said support portion comprising the majority of said toroid, whereby, said spinal support is secured around the waist of a person by means of said first and second mating ends of said belt portion with said median portion of said padded support portion adjacent the lumbar area of the person, and said left and right side portions of said padded portion respectively adjacent the left and right sides of the waist area of the person, thereby providing additional support between the lumbar area and the left and right sides of the waist area of the person and the surface to prevent sagging while the person is reclining on the surface for spinal alignment.

11. The spinal support of claim 10 wherein:
said first pad pocket has a narrower width than said second pad pocket.

12. The spinal support of claim 10 wherein:
each said support pad is formed of a different material.

13. The spinal support of claim 10 wherein:
at least one said support pad has a lenticular cross sectional shape.

14. The spinal support of claim 10 wherein:
each said support pad has a lenticular cross sectional shape.

* * * * *